(12) United States Patent
Pilot-Matias et al.

(10) Patent No.: US 9,044,480 B1
(45) Date of Patent: *Jun. 2, 2015

(54) COMPOSITIONS AND METHODS FOR TREATING HCV

(75) Inventors: Tami Pilot-Matias, Green Oaks, IL (US); Isabelle A. Gaultier, Libertyville, IL (US); Rakesh L. Tripathi, Palatine, IL (US); Christine A. Collins, Skokie, IL (US); Daniel E. Cohen, Highland Park, IL (US); Barry M. Bernstein, Mequon, WI (US)

(73) Assignee: AbbVie Inc., North Chicago, IL (US)

( * ) Notice: Subject to any disclaimer, the term of this patent is extended or adjusted under 35 U.S.C. 154(b) by 380 days.

This patent is subject to a terminal disclaimer.

(21) Appl. No.: 13/412,167

(22) Filed: Mar. 5, 2012

Related U.S. Application Data

(60) Provisional application No. 61/449,002, filed on Mar. 3, 2011, provisional application No. 61/516,304, filed on Apr. 1, 2011.

(51) Int. Cl.
  *A61K 38/00* (2006.01)
  *A61K 31/33* (2006.01)
  *A61K 31/44* (2006.01)
  *A61K 31/497* (2006.01)

(52) U.S. Cl.
  CPC .................................. *A61K 31/497* (2013.01)

(58) Field of Classification Search
  CPC .............................. A61K 38/06; A61K 38/55
  USPC ..................................... 514/3.7, 4.3, 183, 298
  See application file for complete search history.

(56) References Cited

U.S. PATENT DOCUMENTS

| | | | |
|---|---|---|---|
| 8,420,596 B2 * | 4/2013 | Ku et al. | 514/3.7 |
| 2010/0144608 A1 | 6/2010 | Ku et al. | |
| 2011/0312973 A1 | 12/2011 | Liepold et al. | |

OTHER PUBLICATIONS

Bartels D.J., et al., "Natural Prevalence of Hepatitis C Virus Variants with Decreased Sensitivity to NS3.4A Protease Inhibitors in Treatment-Naive Subjects," The Journal of Infectious Diseases, 2008, vol. 198 (6), pp. 800-807.

Fiedler., "Encyclopedia of Excipients for Pharmaceuticals, Cosmetics and related Areas," 5th Edition, Hoepfner E.M., et al., eds., Editio Cantor Verlag Aulendorf, 2002, Table of Contents.

Ge D., et al., "Genetic Variation in IL28B Predicts Hepatitis C Treatment-Induced Viral Clearance," Nature, 2009, vol. 461 (7262), pp. 399-401.

Le Pogam S., et al., Low Rate of Viral Load Rebound Observed Among Treatment-Naive Genotype 1 Patients with Chronic Hepatitis C Treated with Danoprevir (RG7227) Plus Peg-IFN a-2a (40KD) (PEGASYS) Plus Ribavirin: Interim Analysis, 61th Annual Meeting of the American Association for the Study of Liver Diseases [online], Oct. 30-Nov. 3, 2010 [retrieved on Sep. 14, 2012]. Retrieved from the Internet< URL: http://www.natap.org/2010/AASLD/AASLD_84.htm>.

(Continued)

*Primary Examiner* — Shengjun Wang
(74) *Attorney, Agent, or Firm* — Xu Zhang

(57) ABSTRACT

The present invention features methods of using Compound I to suppress HCV mutants, treat treatment-experienced HCV patients, and treat HCV patients having non-CC IL28B rs12979860 genotype.

9 Claims, 2 Drawing Sheets
(2 of 2 Drawing Sheet(s) Filed in Color)

(56) References Cited

OTHER PUBLICATIONS

Lu L., et al., "Mutations Conferring Resistance to a Potent Hepatitis C Virus Serine Protease Inhibitor in Vitro," Antimicrobial Agents and Chemotherapy, 2004, vol. 48 (6), pp. 2260-2266.

Manns M.P., et al., MK-7009 Significantly Improves Rapid Viral Response (RVR) in Combination with Pegylated Interferon Alfa-2a and Ribavirin in Patients with Chronic Hepatitis C (CHC) Genotype 1 Infection, EASL 44th Annual Meeting [online], Apr. 22-26, 2009 [retrieved on Sep. 14, 2012]. Retrieved from the Internet:< URL: http://www.natap.org/2009/EASL/EASL_27.htm>.

Masters K., "Spray Drying Handbook" 4th Edition, John Wiley & Sons, 1985, Table of Contents.

Polymer Handbook, Brandrup J., et al., Eds., Interscience Publishers, 1975, Table of Contents, III-139-III-192.

Salloum S., et al., "The Resistance Mutation R155K in the NS3/4A Protease of Hepatitis C Virus also Leads the Virus to Escape from HLA-A*68-Restricted CD8 T Cells," Antiviral Research, 2010, vol. 87 (2), pp. 272-275.

Sperling L. H., "Introduction to Physical Polymer Science," 2nd Edition, John Wiley & Sons, Inc., 1992, Table of Contents.

Thompson A.J., et al., "Interleukin-28B Polymorphism Improves Viral Kinetics and is the Strongest Pretreatment Predictor of Sustained Virologic Response in Genotype 1 Hepatitis C Virus," Gastroenterology, 2010, vol. 139 (1), pp. 120-129.

Zhou Y., et al., "Phenotypic and Structural Analyses of Hepatitis C Virus NS3 Protease Arg155 Variants: Sensitivity to Telaprevir (VX-950) and Interferon Alpha," The Journal of Biological Chemistry, 2007, vol. 282 (31), pp. 22619-22628.

\* cited by examiner

COMPOSITIONS AND METHODS FOR TREATING HCV

COMPOSITIONS AND METHODS FOR TREATING HCV

This application claims priority from U.S. Provisional Application No. 61/449,002 filed Mar. 3, 2011, and U.S. Provisional application No. 61/516,304 filed Apr. 1, 2011.

Inventions described in this application were made by or on behalf of Abbott Laboratories and Enanta Pharmaceuticals, Inc. whom are parties to a joint research agreement, that was in effect on or before the date such inventions were made and such inventions were made as a result of activities undertaken within the scope of the joint research agreement.

FIELD OF THE INVENTION

The present invention relates to compositions and methods useful for treating HCV infection.

BACKGROUND

The hepatitis C virus (HCV) is an RNA virus belonging to the *Hepacivirus* genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The drawings are provided for illustration, not limitation.

DETAILED DESCRIPTION

Figure 1:
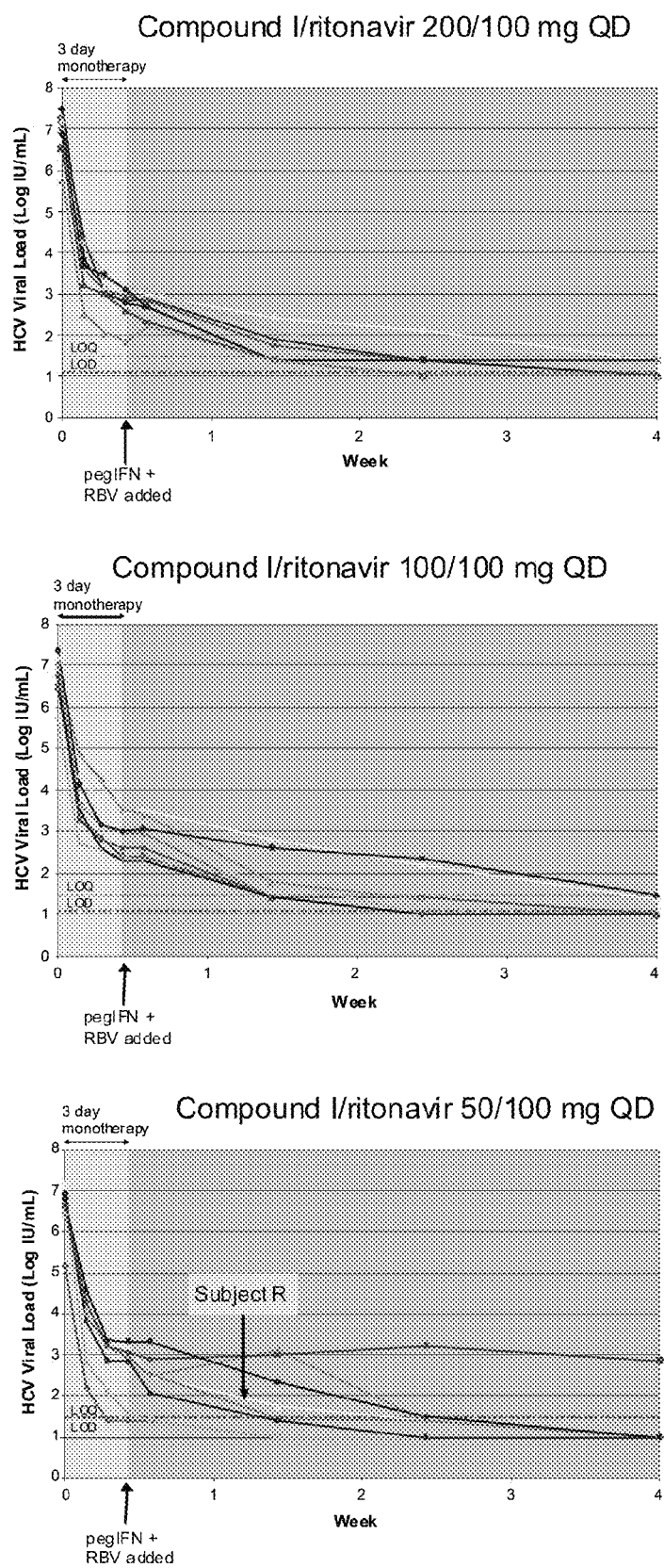
FIG. 1 shows viral load decline curves for individual subjects in each of Compound I/ritonavir dose groups.
Figure 2:
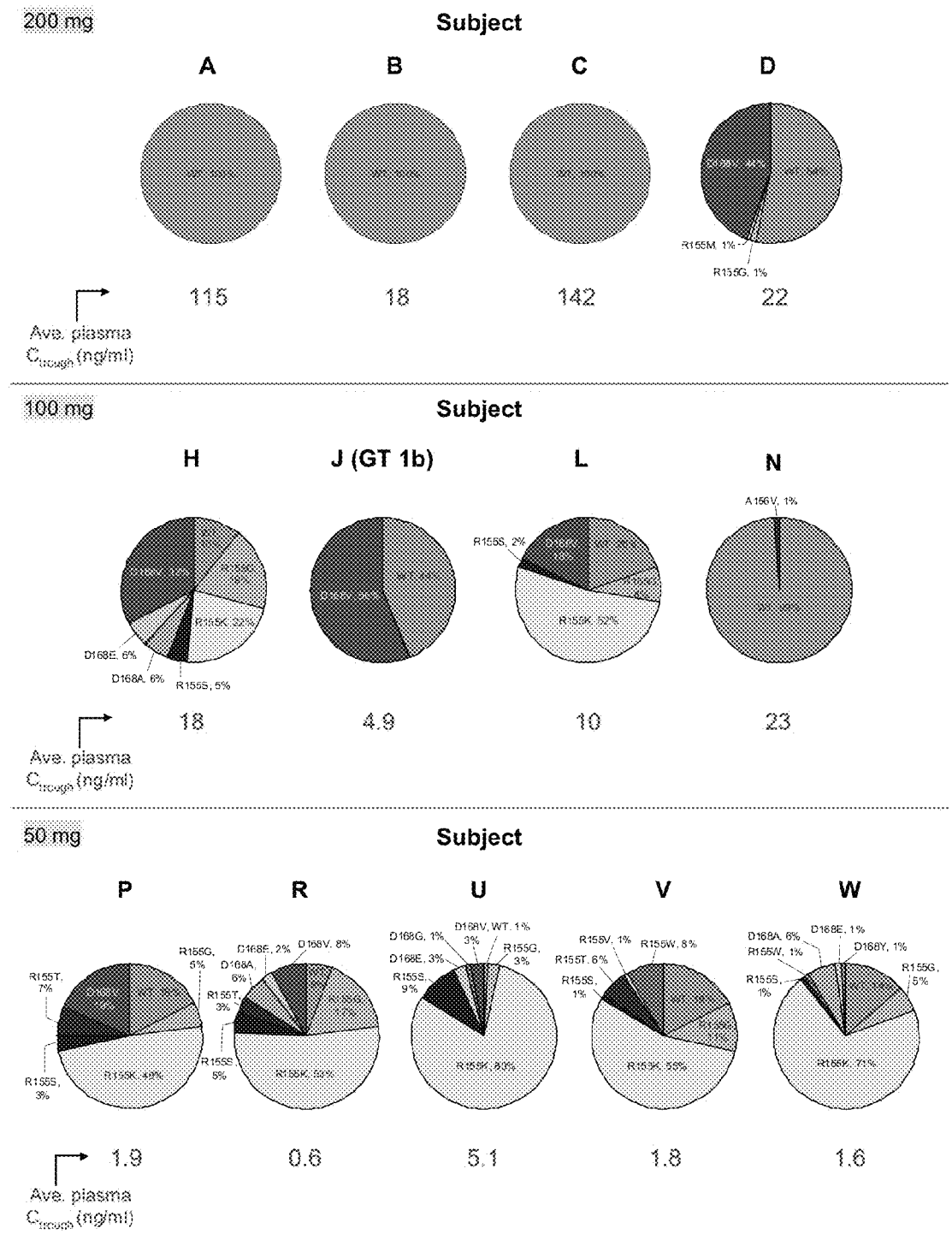
FIG. 2 is clonal sequence analysis of samples obtained from subjects dosed with 50/100, 100/100, or 200/100 mg Compound I/ritonavir after 3 days of monotherapy.

The present invention features methods of using (2R,6S,13aS,14aR,16aS,Z)—N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound I), or a pharmaceutically acceptable salt thereof, to treat HCV infection. Compound I is a potent HCV protease inhibitor, the synthesis and formulation of which are described in U.S. Patent Application Publication No. 20100144608, U.S. Provisional Application Ser. No. 61/339,964 filed on Mar. 10, 2010, and U.S. patent application Ser. No. 13/042,805 filed on Mar. 8, 2011 and now U.S. Patent Application Publication No. 20110312973. All of these applications are incorporated herein by reference in their entireties.

It was unexpectedly discovered that Compound I can significantly suppress the emergence of certain HCV genotype 1 resistant mutants, e.g., genotype 1 R155 or D168 resistant mutants, such as R155K, D168V, R155S, R155T, R155G, R155W, A156V, D168E, D168A, D168G, D168E or D168Y mutants, and in particular R155K and D168V mutants. Clinical trials and replicon cell assays have identified HCV variants that are resistant to many known protease inhibitors. For instance, the R155K mutation has been shown to confer low-level resistance to telaprevir and boceprevir and confer high-level resistant to BILN 2061 and danoprevir (ITMN-191). See Bartels et al., The Journal of Infectious Diseases 198:800-807 (2008). See also Lu et al., Antimicrobial Agents and Chemotherapy, 48:2260-2266 (2004); and Zhou et al., The Journal of Biological Chemistry, 282:22619-22628 (2007). Viral load rebound, which often indicates treatment failure, has been observed in patients receiving treatment with danoprevir after the R155K resistant mutant emerges. See www-.natap.org/2010/AASLD/AASLD_84.htm (61th Annual Meeting of the American Association for the Study of Liver Diseases, Boston, Mass., Oct. 30-Nov. 3, 2010). Likewise, viral load rebound has been reported in patients receiving treatment with vaniprevir (MK-7009). R155K or D168V mutants have been detected in these patients, suggesting resistance or reduced susceptibility of these mutations to vaniprevir. See www.natap.org/2009/EASL/EASL_27.htm (EASL 44th Annual Meeting, April 2009, Copenhagen, Denmark). Moreover, HCV variants harboring the resistant mutation R155K have been detected as the predominant quasispecies in some treatment-naïve patients. See Salloum et al., Antiviral Research 87:272-275 (2010). Accordingly, with significantly improved inhibitory activities against wild-type as well as the emergence of mutant strains, Compound I enables an effective and broad-spectrum treatment for HCV infections.

It was also unexpectedly found that patients with IL28B rs12979860 CC or non-CC genotypes achieve similar virologic response to Compound I when used in combination with peginterferon and ribavirin. Recent studies have shown that a single nucleotide polymorphism (SNP) 3 kilobases upstream of the IL28B gene, rs12979860, predicts HCV viral clearance and virologic response to peginterferon+ribavirin (P/R) treatment in HCV-infected patients. Patients with rs12979860 CC genotype have higher treatment success rates with P/R than those with CT or TT genotypes. See Ge et al., NATURE 461 (7262):399-401 (2009); and Thompson et al., GASTROENTEROLOGY 139(1):120-129 (2010). Several studies showed that when treated with P/R, the HCV virus was eradicated in about 80% of CC genotype patients, compared to only about 25% of those with TT genotype, while the CT genotype response was intermediate.

Accordingly, in one aspect, the present invention features methods of treating a HCV patient who is prone to the emergence of resistant mutations or harbors a resistant mutant. The methods comprise administering to said patients at least 150 mg/day of Compound I or a pharmaceutically acceptable salt thereof, together with at least 50 mg/day of ritonavir or a pharmaceutically acceptable salt. Preferably, the methods comprise administering to said patients at least 150 mg/day of Compound I or a pharmaceutically acceptable salt thereof, together with at least 100 mg/day of ritonavir or a pharmaceutically acceptable salt. More preferably, the methods comprise administering to said patients 200 mg/day of Compound I or a pharmaceutically acceptable salt thereof, together with at least 100 mg/day of ritonavir or a pharmaceutically acceptable salt. Compound I and ritonavir can be administered simultaneously or sequentially. They can be administered in separate dosage forms, or preferably be co-formulated in a single dosage form. Other cytochrome P450 inhibitor such as cobicistat can be used in lieu of ritonavir.

Prior to the treatment, the HCV patient may harbor, without limitation, genotype 1 R155 or D166 resistant mutations, such as R155K, D168V, R155S, R155T, R155G, R155W, A156V, D168E, D168A, D168G, D168E or D168Y mutants. Preferably, the patient may harbor, without limitation, R155K or D168V resistant mutants. Or, the HCV patient may be prone to the emergence of these resistant mutants. As used herein, HCV patients are prone to the emergence of resistant mutants if they have the tendency to have resistant mutations when treated with another protease inhibitor, such as telaprevir, boceprevir, danoprevir, vaniprevir, narlaprevir, TMC-435 (Tibotec), BILN 2061 (Boehringer Ingelheim), or BI-201335 (Boehringer Ingelheim). This tendency may lead to treatment failure for those other protease inhibitors. The patient being treated according to this aspect of the invention can be, without limitation, a treatment-naïve patient.

In another aspect, the present invention features methods of treating treatment-experienced HCV patients. These patients often have failed the prior treatment due to the appearance of resistant mutants or the ineffectiveness of the prior drugs used (e.g., a regimen using a different HCV protease inhibitor than Compound I). Sometimes, the HCV strains in these patients can return to wild type after termination of the prior treatment. Because Compound I is effective in suppressing the appearance of resistant mutations, the present invention features the use of Compound I or a salt thereof to treat treatment-experienced patients. These methods comprise administering to a treatment-experienced patient at least 150 mg/day (e.g., 150 or preferably 200 mg/day) of Compound I or a pharmaceutically acceptable salt thereof, together with at least 50 mg/day of ritonavir or a pharmaceutically acceptable salt. Preferably, the prior treatment did not sufficiently suppress the level of HCV in the blood of said patient either due to less effectiveness in inhibiting the HCV virus or the appearance of resistant mutants. For instance, the prior treatment may only reduce the blood level of HCV in the patient by less than 10-fold; or during the prior treatment, at least one HCV resistant mutation (e.g., a mutation at R155 or D158, such as R155K or D168V) appears and thereby makes the treatment ineffective. Also preferably, the unsuccessful prior treatment uses a different HCV protease inhibitor than Compound I. For example, the prior treatment can use a protease inhibitor selected from telaprevir, boceprevir, narlaprevir, TMC-435 (Tibotec), BI-201335 (Boehringer Ingelheim), danoprevir, vaniprevir, or BMS-650032 (BMS). More preferably, the methods comprise administering to a treatment-experienced patient 200 mg/day of Compound I or a pharmaceutically acceptable salt thereof, and 100 mg/day of ritonavir or a pharmaceutically acceptable salt. Other cytochrome P450 inhibitor such as cobicistat can be used in lieu of ritonavir.

In yet another aspect, the present invention features methods of treating patients having non-CC IL28B rs12979860 genotype. The methods comprise administering to such a patient at least 150 mg/day of Compound I or a pharmaceutically acceptable salt thereof, together with at least 50 mg/day of ritonavir or a pharmaceutically acceptable salt. Preferably, the methods comprise administering to such a patient at least 200 mg/day of Compound I or a pharmaceutically acceptable salt thereof, together with at least 100 mg/day of ritonavir or a pharmaceutically acceptable salt. Other cytochrome P450 inhibitor such as cobicistat can be used in lieu of ritonavir.

A treatment method of the invention may last, for example and without limitation, at least 24 weeks, 48 weeks, or even longer. Preferably, after the 24-week or 48-week treatment, the patient does not have any detectable or newly-generated HCV resistant mutants, such as HCV mutations at R155, D168 or both (e.g., HCV strains with R155K, D168V or both mutations). The patient can be infected with, without limitation, HCV genotype 1 (e.g., 1a or 1b).

In the methods of the present invention, ribavirin can be administered, for example, daily, and interferon can be administered, for example, weekly, to the patient during the treatment period. Suitable interferon for this purpose include, but are not limited to, α-interferon, β-interferon, pegylated interferon-α, and pegylated interferon-lambda. Preferably, peginterferon alfa-2a (e.g., PEGASYS, Roche) is used.

Moreover, any method of the present invention can employ Compound I, or a salt thereof, together with at least another anti-HCV agent selected from a HCV polymerase inhibitor, a NS5A inhibitor, a cyclophilin inhibitor, a CD81 inhibitor, or an internal ribosome entry site inhibitor. Preferably, the other anti-HCV agent is selected from a non-nucleoside HCV polymerase inhibitor, a nucleotide HCV polymerase inhibitor, or a NS5A inhibitor. More preferably, the other anti-HCV agent is selected from the group consisting of: telaprevir, boceprevir, narlaprevir, TMC-435 (Tibotec), BI-201335 (Boehringer Ingelheim), danoprevir, vaniprevir, BMS-650032 (BMS), alisporovir, BMS-790052 (BMS), BMS-824383 (BMS), PPI-461 (Presidio), ANA-598 (Anadys), filibuvir, tegobuvir, VX-222 (VCH-222) (Vertex & ViraChem), PSI-938 (Pharmasset), RG7128 (Roche), PSI-7977 (Pharmasset), IDX-184 (Idenix), TMC64912 (Medivir), ACH-1625 (Archillion), ACH-1095 (Archillion), ACH-2684 (Archillion), ANA773 (Anadys), VBY-376 (Virobay), VX-500 (Vertex), VX-916 (Vertex), VX-759 (Vertex), IDX136 (Idenix), IDX316 (Idenix), VX-813 (Vertex), IDX-PI (Novartis), PSI-7851 (Pharmasset), MK-3281 (Merck), IDX-375 (Idenix), BILB-1941 (Boehringer Ingelheim), INX-189 (Inhibitex), GS-9256 (Gilead), PHX-1766, AVL-181 (Avila), AVL-192 (Avila), INX08189 (Inhibitex), GSK625433 (GlaxoSmithKline), AZD7295 (Arrow), PPI-461 (Presidio), PPI-1301 (Presidio), ACH-2684 (Achillion), ACH-2928 (Achillion), GS-9190 (Gilead), IDX-320 (Idenix), ITX-4520 (iTherx), ITX-5061 (iTherx), VCH-759 (ViroChem), BMS-824393 (BMS), BMS-791325 (BMS), BI-207127 (BMS), PF-868554 (Pfizer), MK-0608 (Merck), CTS-1027 (Conatus), and any combination thereof. For example, Compound I can be combined with one or more non-nucleoside HCV polymerase inhibitors (e.g., a non-nucleoside inhibitor described above). For another example, Compound I can be combined with one or more nucleotide HCV polymerase inhibitors (e.g., a nucleoside inhibitor described above). For yet another example, Compound I can be combined with one or more HCV NS5A inhibitors (e.g., a NS5A inhibitor described above). For still yet another example, Compound I can be combined with one or more non-nucleoside HCV polymerase inhibitors and one or more HCV NS5A inhibitors. For yet another example, Compound I can be combined with one or more nucleoside HCV polymerase inhibitors and one or more HCV NS5A inhibitors. For another example, Compound I can be combined with one or more non-nucleoside HCV polymerase inhibitors, one or more nucleoside HCV polymerase inhibitors, and one or more HCV NS5A inhibitors.

Compound I and the other anti-HCV agent can be administered simultaneously or sequentially. They can be formulated in a single dosage form, or separately formulated in different dosage forms. They can also be separately formulated but co-packaged.

When used in a method of the present invention, Compound I or salt thereof, and ritonavir or salt thereof, preferably are co-formulated in a single dosage form. For instance, such a dosage form can comprise 150 mg Compound I or a salt thereof, and 100 mg ritonavir or a salt thereof. For another instance, such a dosage form can comprise 200 mg Compound I or a salt thereof, and 100 mg ritonavir or a salt thereof. Preferably, such a dosage form comprises 150 mg Compound I and 100 mg ritonavir. More preferably, such a dosage form comprises 200 mg Compound I and 100 mg ritonavir. Compound I and ritonavir can also be formulated in different dosage forms.

Preferably, the patient is administered with the above dosage form once daily.

Preferably, the dosage form used in a method of the present invention is a solid composition which comprises (1) Compound I (or a pharmaceutically acceptable salt thereof) in an amorphous form and (2) ritonavir (or a pharmaceutically acceptable salt thereof) in an amorphous form, and optionally (3) a pharmaceutically acceptable hydrophilic polymer and a pharmaceutically acceptable surfactant.

In one aspect, the dosage form employed in a method of the present invention is a solid composition comprising a solid dispersion, wherein the solid dispersion comprises Compound I (or a pharmaceutically acceptable salt thereof) in an amorphous form and a pharmaceutically acceptable hydrophilic polymer, and the solid composition further comprises a pharmaceutically acceptable surfactant. The surfactant can be, without limitation, either formulated in the solid dispersion or separately combined or mixed with the solid dispersion. Preferably, the hydrophilic polymer has a $T_g$ of at least 50° C. More preferably, the hydrophilic polymer has a $T_g$ of at least 80° C. Highly preferably, the hydrophilic polymer has a $T_g$ of at least 100° C. Also preferably, the surfactant has a HLB value of at least 10. Hydrophilic polymers with $T_g$ of at least 25° C. can also be used.

In one embodiment of this aspect of the invention, the hydrophilic polymer is selected from homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, or polysaccharide. Non-limiting examples of suitable hydrophilic polymers include homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, or xanthan gum.

In another embodiment of this aspect of the invention, the surfactant is selected from polyoxyethylene castor oil derivates, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, or sorbitan fatty acid mono ester. Non-limiting examples of suitable surfactants include polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40, also known as polyoxyl 40 hydrogenated castor oil or macrogolglycerol hydroxystearate) or polyethylenglycol 60 hydrogenated castor oil (Cremophor® RH 60), mono fatty acid ester of polyoxyethylene sorbitan, such as mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40) or polyoxyethylene (20) sorbitan monolaurate (Tween® 20), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate, sucrose monostearate, sucrose distearate, sucrose monolaurate, sucrose dilaurate, sorbitan mono laurate, sorbitan monooleate, sorbitan monopalmitate, or sorbitan stearate.

In yet another embodiment, the solid dispersion is an amorphous solid dispersion. In still another embodiment, the solid dispersion is an amorphous solid dispersion which comprises Compound I (or a pharmaceutically acceptable salt thereof), the hydrophilic polymer, and the surfactant. In a further embodiment, the solid dispersion is a solid solution comprising Compound I (or a pharmaceutically acceptable salt thereof) and the hydrophilic polymer. In yet another embodiment, the solid dispersion is a solid solution comprising Compound I (or a pharmaceutically acceptable salt thereof), the hydrophilic polymer and the surfactant.

In yet another embodiment of this aspect of the invention, the hydrophilic polymer is a homopolymer or copolymer of N-vinyl pyrrolidone. Preferably, the hydrophilic polymer is copovidone.

In still another embodiment, the surfactant is propylene glycol laurate (e.g., lauroglycol FCC from Gattefosse). The solid composition may further comprise another pharmaceutically acceptable surfactant such as D-alpha-tocopheryl polyethylene glycol 1000 succinate (vitamin E TPGS).

In still yet another embodiment, the surfactant is a polysorbate. Preferably, the surfactant is polysorbate 80 (Tween 80).

In yet another embodiment, a solid composition used in a method of the invention comprises an amorphous solid dispersion or a solid solution which comprises Compound I (or a pharmaceutically acceptable salt thereof), copovidone, and a surfactant selected from polysorbate (preferably polysorbate 80), vitamin E TPGS or a combination of vitamin E TPGS and propylene glycol laurate (e.g., lauroglycol FCC).

A solid composition used in the present invention may further include ritonavir, preferably a solid dispersion of ritonavir. Ritonavir and Compound I (or a pharmaceutically acceptable salt thereof) may be formulated in the same solid dispersion or solid solution; they may be also formulated in different solid dispersions or solid solutions.

A solid composition employed in the invention may further comprise another anti-HCV agent, for example, an agent selected from HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

Compound I has low aqueous solubility, and its in vivo absorption is expected to be dissolution-rate limited. Formulating Compound I in an amorphous form can increase the inherent drug solubility and dissolution rate, thereby enhancing the bioavailability of the compound. A solid composition used in the invention can also include ritonavir. Ritonavir is a potent inhibitor of cytochrome P450 3A4 enzyme (CYP3A4), and CYP3A4 is believed to be involved in the metabolism of Compound I. Therefore, co-administering Compound I with ritonavir can reduce the metabolism of Compound I, thereby improving the bioavailability of Compound I. Other cytochrome P450 3A4 enzyme inhibitors such as cobicistat can be used as well in the methods of the invention.

A non-limiting way to form an amorphous form of Compound I or a combination of Compound I and ritonavir is through the formation of solid dispersions with a polymeric carrier. The presence of hydrophilic polymer(s) and surfactant(s), as well as the dispersion of Compound I in an amorphous form in a matrix containing the polymer(s), can significantly enhance the dissolution rate of the poorly soluble Compound I. In many cases, a solid dispersion formulation can also effectively maintain Compound I in its supersaturation state to allow for better absorption.

As used herein, the term "solid dispersion" defines a system in a solid state (as opposed to a liquid or gaseous state) comprising at least two components, wherein one component is dispersed throughout the other component or components. For example, an active ingredient or a combination of active ingredients can be dispersed in a matrix comprised of a pharmaceutically acceptable hydrophilic polymer(s) and a pharmaceutically acceptable surfactant(s). The term "solid dispersion" encompasses systems having small particles of one phase dispersed in another phase. These particles are often of less than 400 µm in size, such as less than 100, 10, or 1 µm in size. When a solid dispersion of the components is such that the system is chemically and physically uniform or homogenous throughout or consists of one phase (as defined in thermodynamics), such a solid dispersion is called a "solid solution." A glassy solution is a solid solution in which a solute is dissolved in a glassy solvent.

The term "$AUC_\infty$" refers to the area under the plasma concentration time curve (AUC) extrapolated to infinity.

The terms "weight percent" or "percent by weight" or "% by weight" or "wt %" denote the weight of an individual component in a composition or mixture as a percentage of the weight of the composition or mixture.

In one aspect, a method of the present invention employs a solid composition comprising Compound I (or a pharmaceutically acceptable salt thereof) in an amorphous form, a pharmaceutically acceptable hydrophilic polymer, and a pharmaceutically acceptable surfactant. Compound I (or the salt thereof) and the polymer are formulated in a solid dispersion. The surfactant may also be formulated in the same solid dispersion; or the surfactant can be separately combined or mixed with the solid dispersion.

In one embodiment of this aspect, the solid composition comprises an amorphous solid dispersion which comprises Compound I (or a pharmaceutically acceptable salt thereof), a pharmaceutically acceptable hydrophilic polymer and a pharmaceutically acceptable surfactant. In another embodiment, the solid composition comprises a solid solution which comprises Compound I (or a pharmaceutically acceptable salt thereof) and a pharmaceutically acceptable hydrophilic polymer. In still another embodiment, the solid composition comprises a solid solution which comprises Compound I (or a pharmaceutically acceptable salt thereof), a pharmaceutically acceptable hydrophilic polymer and a pharmaceutically acceptable surfactant. In yet another embodiment, the solid composition comprises a glassy solution which includes Compound I (or a pharmaceutically acceptable salt thereof) and a pharmaceutically acceptable hydrophilic polymer. In a further embodiment, the solid composition comprises a glassy solution which includes Compound I (or a pharmaceutically acceptable salt thereof), a pharmaceutically acceptable hydrophilic polymer and a pharmaceutically acceptable surfactant.

A solid composition employed in the invention can further comprise a solid dispersion of ritonavir (or a pharmaceutically acceptable salt thereof). Preferably, the solid composition comprises a solid solution of ritonavir (or a pharmaceutically acceptable salt thereof). More preferably, the solid composition comprises a glassy solution of ritonavir (or a pharmaceutically acceptable salt thereof). Compound I (or a pharmaceutically acceptable salt thereof) and ritonavir (or a pharmaceutically acceptable salt thereof) can be formulated in the same solid dispersion or solid solution. They may also be formulated in separate solid dispersions or solid solutions, which can then be combined or mixed to form a solid composition of the present invention.

In yet another embodiment, a solid composition used in the present invention comprises an amorphous solid dispersion which includes Compound I (or a pharmaceutically acceptable salt thereof), ritonavir (or a pharmaceutically acceptable salt thereof) and a pharmaceutically acceptable hydrophilic polymer. In another embodiment, the solid composition comprises an amorphous solid dispersion which includes Compound I (or a pharmaceutically acceptable salt thereof), ritonavir (or a pharmaceutically acceptable salt thereof), a pharmaceutically acceptable hydrophilic polymer and a pharmaceutically acceptable surfactant. In still another embodiment, the solid composition comprises a solid solution which includes Compound I (or a pharmaceutically acceptable salt thereof), ritonavir (or a pharmaceutically acceptable salt thereof), and a pharmaceutically acceptable hydrophilic polymer. In still yet another embodiment, the solid composition comprises a solid solution which includes Compound I (or a pharmaceutically acceptable salt thereof), ritonavir (or a pharmaceutically acceptable salt thereof), a pharmaceutically acceptable hydrophilic polymer and a pharmaceutically acceptable surfactant.

In yet another embodiment, a solid composition employed in the invention comprises a first amorphous solid dispersion which includes Compound I (or a pharmaceutically acceptable salt thereof) and a pharmaceutically acceptable hydrophilic polymer, and a second amorphous solid dispersion comprising ritonavir (or a pharmaceutically acceptable salt thereof). In another embodiment, the solid of the invention comprises a first amorphous solid dispersion which includes Compound I (or a pharmaceutically acceptable salt thereof), a pharmaceutically acceptable hydrophilic polymer and a pharmaceutically acceptable surfactant, and a second amorphous solid dispersion comprising ritonavir (or a pharmaceutically acceptable salt thereof). In still another embodiment, the solid composition comprises a first solid solution which includes Compound I (or a pharmaceutically acceptable salt thereof) and a pharmaceutically acceptable hydrophilic polymer, and a second solid solution comprising ritonavir (or a pharmaceutically acceptable salt thereof). In another embodiment, the solid composition comprises a first solid solution which includes Compound I (or a pharmaceutically acceptable salt thereof), a pharmaceutically acceptable hydrophilic polymer and a pharmaceutically acceptable surfactant, and a second solid solution comprising ritonavir (or a pharmaceutically acceptable salt thereof).

Preferably, a solid dispersion or solid solution that contains ritonavir also includes a pharmaceutically acceptable surfactant to improve the dissolution and/or bioavailability of ritonavir.

The weight ratio of Compound I over ritonavir in a solid composition of the invention may range, without limitation, from 1:1 to 5:1. Preferably, the weight ratio of Compound I over ritonavir is 2:1, 3:1, or 4:1.

A solid composition employed in the invention can contain, for example, from 1 to 50% by weight of Compound I. For instance, the solid composition can contain from 5 to 30% by weight of Compound I. Preferably, a solid composition employed in the invention contains from 10 to 25% by weight of Compound I.

A solid dispersion employed in the invention may contain at least 30% by weight of a pharmaceutically acceptable hydrophilic polymer or a combination of such hydrophilic polymers. Preferably, the solid dispersion contains at least 40% by weight of a pharmaceutically acceptable hydrophilic polymer or a combination of such hydrophilic polymers. More preferably, the solid dispersion contains at least 50% (including, e.g., at least 60%, 70% or 80%) by weight of a pharmaceutically acceptable hydrophilic polymer or a combination of such polymers. A solid dispersion employed in the invention may also contain at least 1% by weight of a pharmaceutically acceptable surfactant or a combination of such surfactants. Preferably, the solid dispersion contains at least 2% by weight of a pharmaceutically acceptable surfactant or a combination of such surfactants. More preferably, the solid dispersion contains from 4% to 20% by weight of the surfactant(s), such as from 5% to 10% by weight of the surfactant(s).

In one embodiment, a solid dispersion employed in the invention comprises at least 30% by weight of a pharmaceutically acceptable hydrophilic polymer or a combination of such polymers, and at least 1% by weight of a pharmaceutically acceptable surfactant or a combination of such surfactants. In another embodiment, a solid dispersion employed in the invention comprises at least 50% by weight of a pharmaceutically acceptable hydrophilic polymer or a combination of such polymers, and from 2% to 20% by weight of a pharmaceutically acceptable surfactant or a combination of such surfactants. In yet another embodiment, a solid dispersion employed in the invention comprises from 50% to 90% by weight of a pharmaceutically acceptable hydrophilic polymer or a combination of such polymers, and from 3% to 15% by weight of a pharmaceutically acceptable surfactant or a combination of such surfactants. In yet another embodiment, a solid dispersion employed in the invention comprises from 60% to 80% by weight of a pharmaceutically acceptable hydrophilic polymer or a combination of such polymers, and from 5% to 10% by weight of a pharmaceutically acceptable surfactant or a combination of such surfactants.

Preferably, a hydrophilic polymer employed in the present invention has a $T_g$ of at least 50° C., more preferably at least 60° C., and highly preferably at least 80° C. including, but not limited to from, 80° C. to 180° C., or from 100° C. to 150° C. Methods for determining $T_g$ values of organic polymers are described in INTRODUCTION TO PHYSICAL POLYMER SCIENCE (2nd Edition by L. H. Sperling, published by John Wiley & Sons, Inc., 1992). The $T_g$ value can be calculated as the weighted sum of the $T_g$ values for homopolymers derived from each of the individual monomers, i.e., the polymer $T_g = \Sigma W_i \cdot X_i$ where $W_i$ is the weight percent of monomer in the organic polymer, and $X_i$ is the $T_g$ value for the homopolymer derived from monomer i. $T_g$ values for the homopolymers may be taken from POLYMER HANDBOOK (2nd Edition by J. Brandrup and E. H. Immergut, Editors, published by John Wiley & Sons, Inc., 1975). Hydrophilic polymers with a $T_g$ as described above may allow for the preparation of solid dispersions that are mechanically stable and, within ordinary temperature ranges, sufficiently temperature stable so that the solid dispersions may be used as dosage forms without further processing or be compacted to tablets with only a small amount of tabletting aids. Hydrophilic polymers having a $T_g$ of below 50° C. may also be used.

Preferably, a hydrophilic polymer employed in the present invention is water-soluble. A solid composition employed in the present invention can also comprise poorly water-soluble or water-insoluble polymer or polymers, such as cross-linked polymers. A hydrophilic polymer comprised in a solid composition preferably has an apparent viscosity, when dissolved at 20° C. in an aqueous solution at 2% (w/v), of 1 to 5000 mPa·s., and more preferably of 1 to 700 mPa·s, and most preferably of 5 to 100 mPa·s.

Hydrophilic polymers suitable for use for the invention include, but are not limited to, homopolymers or copolymers of N-vinyl lactams, such as homopolymers or copolymers of N-vinyl pyrrolidone (e.g., polyvinylpyrrolidone (PVP), or copolymers of N-vinyl pyrrolidone and vinyl acetate or vinyl propionate); cellulose esters or cellulose ethers, such as alkylcelluloses (e.g., methylcellulose or ethylcellulose), hydroxyalkylcelluloses (e.g., hydroxypropylcellulose), hydroxyalkylalkylcelluloses (e.g., hydroxypropylmethylcellulose), and cellulose phthalates or succinates (e.g., cellulose acetate phthalate and hydroxypropylmethylcellulose phthalate, hydroxypropylmethylcellulose succinate, or hydroxypropylmethylcellulose acetate succinate); high molecular polyalkylene oxides, such as polyethylene oxide, polypropylene oxide, and copolymers of ethylene oxide and propylene oxide; polyacrylates or polymethacrylates, such as methacrylic acid/ethyl acrylate copolymers, methacrylic acid/methyl methacrylate copolymers, butyl methacrylate/2-dimethylaminoethyl methacrylate copolymers, poly (hydroxyalkyl acrylates), and poly(hydroxyalkyl methacrylates); polyacrylamides; vinyl acetate polymers, such as copolymers of vinyl acetate and crotonic acid, and partially hydrolyzed polyvinyl acetate (also referred to as partially saponified "polyvinyl alcohol"); polyvinyl alcohol; oligo- or polysaccharides, such as carrageenans, galactomannans, and xanthan gum; polyhydroxyalkylacrylates; polyhydroxyalkyl-methacrylates; copolymers of methyl methacrylate and acrylic acid; polyethylene glycols (PEGs); or any mixture thereof.

Non-limiting examples of preferred hydrophilic polymers for the invention include polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, and poloxamer 407.

Of these, homopolymers or copolymers of N-vinyl pyrrolidone, such as copolymers of N-vinyl pyrrolidone and vinyl acetate, are preferred. A non-limiting example of a preferred polymer is a copolymer of 60% by weight of N-vinyl pyrrolidone and 40% by weight of vinyl acetate. Other preferred polymers include, without limitation, hydroxypropyl methylcellulose (HPMC, also known as hypromellose in USP), such as hydroxypropyl methylcellulose grade E5 (HPMC-E5); and hydroxypropyl methylcellulose acetate succinate (HPMC-AS).

A pharmaceutically acceptable surfactant employed in the present invention is preferably a non-ionic surfactant. More preferably, a solid composition of the present invention comprises a pharmaceutically acceptable surfactant having an HLB value of at least 10. A solid composition employed in the present invention can also include a mixture of pharmaceutically acceptable surfactants, with at least one surfactant having an HLB value of no less than 10 and at least another surfactant having an HLB value of below 10. In one example, each surfactant comprised in a solid composition has an HLB value of at least 10. In another example, each surfactant comprised in a solid composition has an HLB value of below 10. In yet another example, a solid composition employed in the present invention includes at least two pharmaceutically acceptable surfactants, one having an HLB value of at least 10 and the other having an HLB value of below 10. The HLB system (Fiedler, H.B., ENCYCLOPEDIA OF EXCIPIENTS, 5$^{th}$ ed., Aulendorf: ECV-Editio-Cantor-Verlag (2002)) attributes numeric values to surfactants, with lipophilic substances receiving lower HLB values and hydrophilic substances receiving higher HLB values.

Non-limiting examples of pharmaceutically acceptable surfactants that are suitable for the present invention include polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40, also known as polyoxyl 40 hydrogenated castor oil or macrogolglycerol hydroxystearate) or polyethylenglycol 60 hydrogenated castor oil (Cremophor® RH 60); or a mono fatty acid ester of polyoxyethylene sorbitan, such as a mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20). Other non-limiting examples of suitable surfactants include polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (Lauroglycol); sucrose fatty acid esters, e.g. sucrose monostearate, sucrose distearate, sucrose monolaurate, sucrose dilaurate; sorbitan fatty acid mono esters such as sorbitan mono laurate (Span® 20), sorbitan monooleate, sorbitan monopalmitate (Span® 40), or sorbitan stearate. Other suitable surfactants include, but are not limited to, block copolymers of ethylene oxide and propylene oxide, also known as polyoxyethylene polyoxypropylene block copolymers or polyoxyethylene polypropyleneglycol, such as Poloxamer® 124, Poloxamer® 188, Poloxamer® 237, Poloxamer® 388, or Poloxamer® 407 (BASF Wyandotte Corp.). As described above, a mixture of surfactants can be used in a solid composition of the present invention.

Non-limiting examples of preferred surfactants for the invention include to polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, and sorbitan monolaurate.

In one embodiment, a solid composition employed in the present invention comprises an amorphous solid dispersion or a solid solution which includes Compound I (or a pharmaceutically acceptable salt thereof) and a pharmaceutically acceptable hydrophilic polymer. The solid composition also includes a pharmaceutically acceptable surfactant which preferably is formulated in the amorphous solid dispersion or solid solution. The hydrophilic polymer can be selected, for example, from the group consisting of homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, and polysaccharide. As a non-limiting example, the hydrophilic polymer is selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, and xanthan gum. Preferably, the hydrophilic polymer is selected from polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, or poloxamer 407. More preferably, the hydrophilic polymer is selected from homopolymers of vinylpyrrolidone (e.g., PVP with Fikentscher K values of from 12 to 100, or PVP with Fikentscher K values of from 17 to 30), or copolymers of 30 to 70% by weight of N-vinylpyrrolidone (VP) and 70 to 30% by weight of vinyl acetate (VA) (e.g., a copolymer of 60% by weight VP and 40% by weight VA). The surfactant can be selected, for example, from the group consisting of polyoxyethyleneglycerol triricinoleate or polyoxyl 35 castor oil (Cremophor® EL; BASF Corp.) or polyoxyethyleneglycerol oxystearate, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, and sorbitan fatty acid mono ester. As a non-limited example, the surfactant is selected from the group consisting of polyethylenglycol 40 hydrogenated castor oil (Cremophor® RH 40, also known as polyoxyl 40 hydrogenated castor oil or macrogolglycerol hydroxystearate), polyethylenglycol 60 hydrogenated castor oil (Cremophor® RH 60), a mono fatty acid ester of polyoxyethylene (20) sorbitan (e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20)), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate, sucrose monostearate, sucrose distearate, sucrose monolaurate, sucrose dilaurate, sorbitan mono laurate, sorbitan monooleate, sorbitan monopalnitate, and sorbitan stearate. Preferably, the surfactant is selected from polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, or sorbitan monolaurate. More preferably, the surfactant is selected from Tween (e.g., Tween 80, 60, 40 or 20) or D-alpha-tocopheryl polyethylene glycol 1000 succinate. The solid composition may also comprise an amorphous solid dispersion or solid solution of ritonavir, and preferably, ritonavir and Compound I (or a pharmaceutically acceptable salt thereof) are formulated in the same amorphous solid dispersion or solid solution.

In another embodiment, a solid composition employed in the present invention comprises an amorphous solid dispersion or solid solution which includes Compound I (or a pharmaceutically acceptable salt thereof) and a homopolymer or copolymer of N-vinyl pyrrolidone (e.g., copovidone). The solid composition also comprises a pharmaceutically acceptable surfactant (e.g., vitamin E TPGS, or polysorbate such as polysorbate 80), wherein the surfactant preferably is formulated in the amorphous solid dispersion or solid solution. The solid composition may also comprise an amorphous solid dispersion or solid solution of ritonavir, and preferably, ritonavir and Compound I (or a pharmaceutically acceptable salt thereof) are formulated in the same amorphous solid dispersion or solid solution.

In yet another embodiment, a solid composition employed in the present invention comprises an amorphous solid dispersion or solid solution which includes Compound I (or a pharmaceutically acceptable salt thereof), copovidone, and a pharmaceutically acceptable surfactant selected from vitamin E TPGS or polysorbate (e.g., polysorbate 80). The amorphous solid dispersion or solid solution may also include another pharmaceutically acceptable surfactant such as propylene glycol laurate (e.g., lauroglycol FCC). The solid composition may comprise an amorphous solid dispersion or solid solution of ritonavir, and preferably, ritonavir and Compound I (or a pharmaceutically acceptable salt thereof) are formulated in the same amorphous solid dispersion or solid solution.

A solid dispersion employed in the present invention preferably comprises or consists of a single-phase (defined in thermodynamics) in which the therapeutic agent (e.g., Compound I and/or ritonavir) and the pharmaceutically acceptable hydrophilic polymer are molecularly dispersed. In such cases, thermal analysis of the solid dispersion using differential scanning calorimetry (DSC) typically shows only one single $T_g$, and the solid dispersion does not contain any detectable crystalline Compound I or ritonavir as measured by X-ray powder diffraction spectroscopy.

A solid composition employed in the present invention can further be administered together with one or more other anti-HCV agents. These other anti-HCV agents can be, for example, HCV polymerase inhibitors (including nucleoside or non-nucleoside type of polymerase inhibitors), HCV protease inhibitors, HCV helicase inhibitors, CD81 inhibitors, cyclophilin inhibitors, internal ribosome entry site inhibitors, or HCV NS5A inhibitors. Specific examples of these other anti-HCV agents include, but are not limited to, telaprevir, boceprevir, ITMN-191, BI-201335, TMC-435, MK-7009, VBY-376, VX-500 (Vertex), PHX-B, ACH-1625, IDX136, IDX316, VX-813 (Vertex), SCH 900518 (Schering-Plough), TMC-435 (Tibotec), ITMN-191 (Intermune, Roche), MK-7009 (Merck), IDX-PI (Novartis), BI-201335 (Boehringer Ingelheim), R7128 (Roche), PSI-7851 (Pharmasset), MK-3281 (Merck), PF-868554 (Pfizer), IDX-184 (Novartis), IDX-375 (Pharmasset), BILB-1941 (Boehringer Ingelheim), GS-9190 (Gilead), BMS-790052 (BMS), and Albuferon (Novartis).

A solid composition employed in the present invention preferably is a common solid oral dosage form. Common solid oral dosage forms suitable for the present invention include, but are not limited to, capsules, dragees, granules, pills, powders and tablets, with capsules and tablets being preferred. A solid oral dosage form employed in the present invention can also include other excipients or inset diluents, such as sucrose, lactose or starch. Lubricants, coloring agents, releasing agents, coating agents, sweetening or flavoring agents, buffering agents, preservatives, or antioxidants can also be included in a solid oral dosage form of the present invention.

A solid composition employed in the present invention can be prepared by a variety of techniques such as, without limitation, melt-extrusion, spray-drying, co-precipitation, freeze drying, or other solvent evaporation techniques, with melt-extrusion and spray-drying being preferred. The melt-extrusion process typically comprises the steps of preparing a melt which includes the active ingredient(s), the hydrophilic polymer(s) and preferably the surfactant(s), and then cooling the melt until it solidifies. "Melting" means a transition into a liquid or rubbery state in which it is possible for one component to get embedded, preferably homogeneously embedded, in the other component or components. In many cases, the polymer component(s) will melt and the other components including the active ingredient(s) and surfactant(s) will dissolve in the melt thereby forming a solution. Melting usually involves heating above the softening point of the polymer(s). The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredient(s) efficiently. In addition, it may be convenient first to melt the polymer(s) and then to mix in and homogenize the active ingredient(s). In one example, all materials except surfactant(s) are blended and fed into an extruder, while the surfactant(s) is molten externally and pumped in during extrusion.

In another example, the melt comprises Compound I and one or more hydrophilic polymers described above, and the melt temperature is in the range of from 100 to 170° C., preferably from 120 to 150° C., and highly preferably from 135 to 140° C.

In yet another example, the melt comprises Compound I, ritonavir and one or more hydrophilic polymers described above. The melt can also include a pharmaceutically acceptable surfactant described above.

In still another example, the melt comprises Compound I, ritonavir, at least another HCV agent described above, and one or more hydrophilic polymers described above. The melt can also include a pharmaceutically acceptable surfactant described above.

To start a melt-extrusion process, the active ingredient(s) (e.g., Compound I, or a combination of Compound I and ritonavir, or a combination of Compound I, ritonavir and at least another anti-HCV agent) can be employed in their solid forms, such as their respective crystalline forms. The active ingredient(s) can also be employed as a solution or dispersion in a suitable liquid solvent such as alcohols, aliphatic hydrocarbons, esters or, in some cases, liquid carbon dioxide. The solvent can be removed, e.g. evaporated, upon preparation of the melt.

Various additives can also be included in the melt, for example, flow regulators (e.g., colloidal silica), binders, lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose. Particularly suitable ones are extruders or kneaders. Suitable extruders include single screw extruders, intermeshing screw extruders or multiscrew extruders, preferably twin screw extruders, which can be corotating or counterrotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt can range from thin to pasty to viscous. Shaping of the extrudate can be conveniently carried out by a calender with two counter-rotating rollers with mutually matching depressions on their surface. The extrudate can be cooled and allow to solidify. The extrudate can also be cut into pieces, either before (hot-cut) or after solidification (cold-cut).

The solidified extrusion product can be further milled, ground or otherwise reduced to granules. The solidified extrudate, as well as each granule produced, comprises a solid dispersion, preferably a solid solution, of the active ingredient(s) in a matrix comprised of the hydrophilic polymer(s) and optionally the pharmaceutically acceptable surfactant(s). Where the granules do not contain any surfactant, a pharmaceutically acceptable surfactant described above can be added to and blended with the granules. The extrusion product can also be blended with other active ingredient(s) and/or additive(s) before being milled or ground to granules. The granules can be further processed into suitable solid oral dosage forms.

In one example, copovidone and one or more surfactants are mixed and granulated, followed by the addition of aerosil, Compound I and ritonavir. The mixture is then milled. The weight ratio of Compound I over ritonavir can range, for example, from 1:1 to 5:1, such as 1:1, 2:1 or 4:1. For instance, the mixture can contain 10% Compound I and 5% ritonavir by weight. For another instance, the mixture can contain 15% Compound I and 7.5% ritonavir by weight. The mixture is then subject to extrusion, and the extrudate thus produced can be milled and sieved for further processing to make capsules or tablets. Surfactant(s) employed in this example can also be added through liquid dosing during extrusion.

In another example, copovidone and one or more surfactants are mixed and granulated, following by the addition of aerosil and Compound I. The mixture, which may contain for example 15% by weight of Compound I, is then milled and extruded. The extrudate thus produced can be further milled and sieved. Ritonavir extrudate can be similarly prepared. Compound I extrudate can be blended with ritonavir extrudate and then co-compressed to make tablets. Preferably, the weight ratio of Compound I over ritonavir in the blend can range, without limitation, from 1:1 to 1:5, such as 1:1, 2:1 or 4:1.

The approach of solvent evaporation, via spray-drying, provides the advantage of allowing for processability at lower temperatures, if needed, and allows for other modifications to the process in order to further improve powder properties. The spray-dried powder can then be formulated further, if needed, and final drug product is flexible with regards to whether capsule, tablet and/or co-formulation with ritonavir is desired.

Exemplary spray-drying processes and spray-drying equipment are described in K. Masters, SPRAY DRYING HANDBOOK (Halstead Press, New York, $4^{th}$ ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This help to ensure that the dried droplets are essentially solid and can form a fine powder and do not stick to the apparatus wall. The spray-dried product can be collected by removing the material manually, pneumatically, mechanically or by other suitable means. The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

Like the solid extrudate described above, the spray dried product contains a solid dispersion, preferably a solid solution, of the active ingredient(s) in a matrix comprised of the hydrophilic polymer(s) and optionally the pharmaceutically acceptable surfactant(s). Where the spray dried product does not contain any surfactant, a pharmaceutically acceptable surfactant described above can be added to and blended with the spray-dried product before further processing.

Before feeding into a spray dryer, the active ingredient(s) (e.g., Compound I, or a combination of Compound I and ritonavir, or a combination of Compound I, ritonavir and at least another anti-HCV agent), the hydrophilic polymer(s), as well as other optional active ingredients or excipients such as the pharmaceutically acceptable surfactant(s), can be dissolved in a solvent. Suitable solvents include, but are not limited to, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets. The solid dispersion can be either directly compressed, or milled or ground to granules or powders before compression. Compression can be done in a tablet press, such as in a steel die between two moving punches. When a solid composition of the present invention comprises Compound I and ritonavir, or Compound I and another anti-HCV agent, it is possible to separately prepare solid dispersions of each individual active ingredient and then blend the optionally milled or ground solid dispersions before compacting. Compound I and other active ingredient(s) can also be prepared in the same solid dispersion, optionally milled and/or blended with other additives, and then compressed into tablets.

At least one additive selected from flow regulators, disintegrants, bulking agents (fillers) and lubricants may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone and cross-linked sodium carboxymethylcellulose. Non-limiting examples of suitable bulking agents (also referred to as "fillers") are lactose, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like.

Various other additives may also be used in preparing a solid composition of the present invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack.

Solid compositions employed in the present invention may also contain several layers, for example laminated or multi-layer tablets. They can be in open or closed form. "Closed dosage forms" are those in which one layer is completely surrounded by at least one other layer.

In order to facilitate the intake of a solid dosage form, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. The film-coat usually includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. polysorbates, and optionally a pigment, e.g. titanium dioxide or iron oxides. The film-coating may also comprise talc as anti-adhesive. Preferably, the film coat accounts for less than 5% by weight of a pharmaceutical composition of the present invention.

The present invention also features use of a solid composition described herein for the manufacture of medicaments for the treatment of HCV infection according to a method of the present invention described above.

In addition, the present invention features solid compositions described herein for the treatment of treatment-experienced HCV patients or for the suppressing of HCV resistant mutants (e.g., HCV strains with a mutation at R155, D168 or both; in particular, HCV strains with R155K and/or D168V mutations).

It should be understood that the above-described embodiments and the following examples are given by way of illustration, not limitation. Various changes and modifications within the scope of the present invention will become apparent to those skilled in the art from the present description.

Example 1

Genotypic and Phenotypic Characterization of NS3 Variants Selected in HCV-Infected Patients Treated with Compound I and Ritonavir (Compound I/r)

Compound I (50, 100 or 200 mg once daily (QD)) was dosed with 100 mg ritonavir (Compound I/r; n=8 per group)

in treatment-naïve subjects infected with genotype (GT) 1 HCV for 3 days, followed by addition of pegylated interferon and ribavirin (pegIFN/RBV) for an additional 12 weeks. Mean maximum HCV RNA decrease was 4.02 log 10 during the 3 day monotherapy. 21 of 24 subjects had HCV RNA<25 IU/mL at 4 weeks. Genotypic and phenotypic analyses of viral isolates from early time points were performed in order to characterize the development of resistance.

Viral RNA was isolated from the plasma of HCV-infected patients at baseline (Day 1) and Day 4 by using an automated (Abbott m2000) or manual (QIAgen QIAamp Viral RNA Mini Kit) method. Amplicons containing the NS3-4A region were generated by RT-PCR, and PCR fragments containing the first 250 amino acids of NS3 were generated in a second round of PCR. The NS3 domain fragment was subsequently cloned into pJET (Fermentas) vector for clonal sequencing or digested with restriction enzymes and cloned into the replicon shuttle vector for phenotypic analysis. The lower limit of detection of the RT-PCR amplification method restricted the analysis to patient samples with HCV RNA levels above ~500-1000 IU/mL.

Phenotypic analyses of clinical samples were also performed. For replicon transient transfection assays, RNA was transcribed from linearized plasmid DNA using a TranscriptAid T7 transcription kit (Fermentas) and 15 μg RNA was electroporated into Huh7-derived cells. For $EC_{50}$ determinations, various concentrations of Compound I were added to cells 1-2 hr after plating and the cells were cultured for 4 days, followed by measurement of luciferase activity with a luciferase assay system kit (Promega). The replication capacity was determined by measuring the luciferase activity of transfected cells after 4 days of culture in the absence of inhibitor and comparing this to the luciferase activity of an inactive replicon after 4 days.

One subject (R) in the Compound I/r 50/100 mg dose group showed an elevated EC50 at baseline, but this did not appear to impact initial response to Compound I/r. Samples from 7 of the 13 subjects had increased EC50 values at day 4 relative to their baseline EC50 values. The change relative to baseline was 3 to 12-fold, with the exception of the single GT 1b subject (J), who had a 368-fold shift. All 7 subjects went on to achieve HCV RNA<25 IU/mL by Week 4. Clonal sequencing results are available from Day 4 samples from 13 subjects.

Known resistance mutations were present in all 7 of the samples that showed EC50 fold shift at day 4. All 5 of the samples from the Compound I/r 50/100 mg dose group had high prevalence of resistance mutations, primarily at R155. 3 of the 4 samples from the 100/100 mg dose group had resistance mutations detected, and these subjects had a higher proportion of mutations at D168 than seen in the 50/100 mg subjects.

Only 1 of the 4 samples from the 200/100 mg dose group had detectable resistance mutations, predominantly D168V. Although this subject had 44% D168V present at Day 4, no shift in EC50 was observed. This is likely due to the poor fitness of the D168V mutant in the GT 1a replicon.

The early appearance of resistant variants was suppressed in the two subjects with the highest Compound I plasma Ctrough levels. Following addition of pegIFN/RBV, high rates of viral suppression were observed in all dose groups despite the appearance of HCV NS3 variants known to confer resistance to Compound I.

Table 1 shows $EC_{50}$ determination of Day 1 (baseline) and Day 4 samples from subjects dosed with Compound I/r cloned into shuttle. Due to the low viral titer at Day 4, HCV RNA could be amplified for resistance testing in only 13 of the 24 subjects. Samples from 7 subjects (shaded cells in Table 1) showed at least a 3-fold EC50 fold shift at day 4 relative to their baseline EC50 value. All 7 of these subjects were in the 50/100 mg or 100/100 mg dose groups. Table 2 illustrates $EC_{50}$ and replication capacity values in the HCV subgenomic replicon system. R155K was the most prevalent mutant observed in the subjects dosed with Compound I/r 50/100 mg R155K and D168V were both seen in the subjects dosed with Compound I/r 100/100 mg. Only one of the subjects from the Compound I/r 200/100 mg dose group had any resistance mutations. No resistance mutations were observed in the 2 subjects with the highest Compound I plasma trough levels (Subjects A and C).

TABLE 1

NS3 protease domain from subjects dosed with Compound I/r cloned into shuttle vector - $EC_{50}$ determination of Day 1 (baseline) and Day 4 samples

| ABT-450/r Dose | Subject | GT | $EC_{50}$(nM) Day 1 | $EC_{50}$(nM) Day 4 | Fold Change |
|---|---|---|---|---|---|
| 200/100 mg | A | 1a | 1.31 | 1.14 | 0.9 |
| | B | 1a | 1.36 | 1.06 | 0.8 |
| | C | 1a | 3.11 | 3.23 | 1.0 |
| | D | 1a | 2.42 | 2.57 | 1.1 |
| | E | 1a | 0.58 | No product | |
| | F | 1b | 0.04 | No product | |
| | G | 1a | 2.68 | No product | |
| 100/100 mg | H | 1a | 1.55 | 10.2 | |
| | I | 1a | 1.43 | No product | |
| | J | 1b | 0.04 | 15.5 | |
| | K | 1b | 0.07 | No product | |
| | L | 1a | 2.80 | 8.84 | |
| | M | 1a | 0.91 | No product | |
| | N | 1a | 0.58 | 0.64 | 1.1 |
| | O | 1b | 0.05 | No product | |
| 50/100 mg | P | 1a | 0.81 | 8.88 | |
| | Q | 1a | 0.68 | No product | |
| | R | 1a | 5.97 | 68.7 | |
| | S | 1b | 0.06 | No product | |
| | T | 1a | 0.45 | No product | |
| | U | 1a | 1.52 | 11.5 | |
| | V | 1a | 1.01 | 1.69 | 1.7 |
| | W | 1a | 1.54 | 9.78 | |

TABLE 2

$EC_{50}$ and replication capacity values in the HCV subgenomic replicon system

| Replicon | Mutant | $EC_{50}$ (nM) | Fold Change | Rep. Capacity |
|---|---|---|---|---|
| GT 1a | WT | 1.19 | | 1 |
| | R155G | 19.2 | 16 | 0.02 |
| | R155K | 51.5 | 43 | 0.27 |
| | D168A | 70.4 | 59 | 0.35 |
| | D168V | 136 | 115 | 0.04 |
| GT 1b | WT | 0.07 | | 1 |
| | D168V | 17.5 | 257 | 1 |

Example 2

The Effect of IL28B Polymorphism on Virologic Response to Treatment with Pegylated Interferon Alpha-2a and Ribavirin (P/R) Added to Compound I/ritonavir (Compound I/r)

In order to determine whether host IL28B rs12979860 genotype affects the response to Compound I/r alone or when combined with peginterferon+ribavirin (P/R), subjects affected with genotype 1 HCV were randomized to receive various doses of Compound I/r or placebo (PBO). Following 3 days of monotherapy, subjects received Compound I/r or placebo at the same dose in combination with pegylated interferon α-2a 180 µg/week+weight-based ribavirin 1000-1200 mg/day (P/R) through week 12. At week 12, Compound I/r or placebo was discontinued and subjects received P/R alone through up to week 48.

HCV RNA was measured using the Roche COBAS TaqMan® v2.0 assay (LLOQ=25 IU/mL and LLOD=10 IU/mL). All subjects randomized to placebo in the study were pooled in this analysis. Intent-To-Treat (ITT) analyses include all subjects who had at least one dose of study drug. For rapid virologic response (RVR) and complete early virologic response (cEVR), subjects missing data at the relevant visit were considered to have failed to suppress HCV RNA. Virologic response was assessed as mean decrease from baseline in HCV RNA (log 10 IU/mL) at each time point by IL28B rs12979860 genotype for each Compound I/r and PBO+P/R, and tests between subjects of IL28B rs12979860 CC genotype versus non-CC performed with ANCOVA with baseline HCV RNA value as covariate and effects for IL28B rs12979860 genotype, treatment, and their interaction. The proportion of subjects with RVR (HCV RNA<25 IU/mL at week 4) or cEVR (HCV RNA<25 IU/mL at week 12) were calculated by IL28B rs12979860 genotype for each Compound I/r+P/R and PBO+P/R, and tests between subjects of IL28B rs12979860 CC versus non-CC genotype performed with Fisher's exact tests.

A blood sample for IL28B genotyping was collected from each subject with their consent. Genomic DNA was isolated from whole blood using the FlexiGene DNA AGF3000 kit (Qiagen, Valencia, Calif.) on an AutogenFlex 3000 (AutoGen, Holliston, Mass.) and IL28B rs12979860 genotype was determined using the Pyrosequencing detection method (Qiagen, Valencia, Calif.).

Similar clinical studies were conducted on two non-nucleoside HCV polymerase inhibitors (NNP-1 and NNP-2). A total of 74 HCV genotype 1-infected treatment-naïve subjects were enrolled and randomized to Compound I/r (n=24), NNP-1 (n=23), NNP-2 (n=16), or placebo (n=11). Twenty-three (31%) subjects had a CC IL28B rs12979860 genotype, and fifty-five (74%) subjects were infected with HCV genotype 1a. A total of 10 subjects discontinued treatment before week 12 (7 non-CC and 3 CC). No subjects discontinued treatment due to Compound I/r-related adverse events.

Through 3 days of monotherapy, subjects taking Compound I/r, NNP-1, or NNP-2 had significantly greater mean maximum HCV RNA decreases from baseline than those receiving placebo. Subjects with IL28B rs12979860 CC genotype had similar HCV RNA decreases from baseline compared with subjects with non-CC genotype (Table 3).

TABLE 3

HCV RNA Results Through Week 12: Mean (SD), log10 IU/mL

| | Placebo + P/R | | Compound I/r + P/R | | NNP-1 + P/R | | NNP-2 +P/R | |
|---|---|---|---|---|---|---|---|---|
| Treatment | Non-CC | CC | Non-CC | CC | Non-CC | CC | Non-CC | CC |
| Monotherapy: Maxmal change through Day 3 | −0.38 (0.13) N = 8 | −0.33 (0.14) N = 3 | −4.00 (0.48) N = 18 | −4.13 (0.20) N = 6 | −1.04 (0.62) N = 13 | −1.52 (0.97) N = 10 | −1.08 (0.54) N = 12 | −0.83 (0.79) N = 4 |
| Change from baseline to Day 18 | −0.68 (0.47) N = 6 | −3.15* (1.90) N = 3 | −5.25 (0.69) N = 18 | −5.50 (0.38) N = 6 | −2.55 (0.99) N = 12 | −4.15* (1.62) N = 10 | −2.94 (1.23) N = 12 | −4.32* (0.51) N = 4 |
| Change from baseline to Week 4 | −1.34 (0.91) N = 6 | −4.21* (3.05) N = 2 | −5.44 (0.71) N = 17 | −5.96 (0.15) N = 6 | −3.21 (1.10) N = 12 | −4.71* (1.71) N = 10 | −3.64 (1.45) N = 12 | −5.17* (0.74) N = 4 |
| Change from baseline to Week 12 | −3.43 (1.07) N = 3 | −6.37* N = 1 | −5.45 (0.69) N = 15 | −6.11 (0.17) N = 6 | −4.61 (1.29) N = 11 | −5.75* (0.77) N = 8 | −5.00 (0.86) N = 12 | −5.37 (0.97) N = 4 |

*P > 0.05 CC versus non-CC within DAA treatment group.

IL28B rs12979860 CC genotype was associated with a significantly greater HCV RNA decrease at day 18, week 4, and week 12 in subjects receiving PBO+P/R or NNP-1+P/R, and at day 18 and week 4 for subjects receiving NNP-2+P/R (Table 3). IL28B rs12979860 genotype did not significantly affect virologic response at any time during treatment with Compound I/r+P/R.

In subjects taking PBO+P/R, Compound I/r+P/R, or NNP-1+P/R, the CC IL28B rs12979860 genotype was not associated with a greater RVR rate compared to subjects with a non-CC genotype taking the same regimen. In contrast, the CC IL28B rs12979860 genotype was associated with a higher likelihood of achieving RVR in subjects taking NNP-2+P/R (Table 4). In subjects taking PBO+P/R, Compound I/r+P/R, NNP-1+P/R, or NNP-2+P/R, the CC IL28B rs12979860 genotype was not associated with a greater cEVR rate compared to subjects with a non-CC genotype taking the same regimen (Table 4)

TABLE 4

Proportion of Subjects with RVR and cEVR among ITT Population, n (%)

| | Placebo + P/R | | Compound I/r + P/R | | NNP-1 + P/R | | NNP-2 + P/R | |
|---|---|---|---|---|---|---|---|---|
| | Non-CC | CC | Non-CC | CC | Non-CC | CC | Non-CC | CC |
| RVR (HCV RNA <25 IU/mL at week 4) | 0/8 (0%) | 1/3 (33%) | 15/16 (89%) | 5/6 (83%) | 1/13 (8%) | 6/10 (60%) | 4/12 (33%) | 4/4 (100%)* |
| cEVR (HCV RNA <25 IU/mL at week 12) | 1/8 (12.5%) | 1/3 (33%) | 16/18 (89%) | 6/6 (100%) | 7/13 (54%) | 8/10 (80%) | 8/12 (67%) | 4/4 (100%) |

*P < 0.05 CC versus non-CC.
ITT = Intent-To-Treat, subjects who prematurely discontinue before time point are included in the analysis as failing to suppress.

In summary, the above studies showed that through 3 days of monotherapy, subjects receiving Compound I/r, NNP-1, or NNP-2 had significantly greater mean maximum HCV RNA decreases from baseline than those receiving placebo, but IL28B rs12979860 genotype was not significantly associated with virologic response. Through 12 weeks, IL28B rs12979860 genotype was associated with virologic response to NNP-1+P/R, NNP-2+P/R and placebo+P/R at several time points during 12 weeks of therapy. No such association was seen among subjects treated with Compound I/r+P/R.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A method of treating a HCV patient harboring R155 or D168 resistant mutants, comprising administering to said patient at least 150 mg/day of Compound I or a pharmaceutically acceptable salt thereof, and at least 50 mg/day of ritonavir or a pharmaceutically acceptable salt.

2. The method of claim 1, wherein said method comprises administering to said patient 200 mg/day of Compound I or a pharmaceutically acceptable salt thereof, and 100 mg/day of ritonavir or a pharmaceutically acceptable salt.

3. The method of claim 1, further comprising administering to said patient another anti-HCV agent selected from: a HCV polymerase inhibitor, a NS5A inhibitor, a cyclophilin inhibitor, a CD81 inhibitor, or an internal ribosome entry site inhibitor.

4. A method of treating a treatment-experienced HCV patient who has failed a prior treatment using another protease inhibitor due to emergence of at least one resistant mutation, the method comprising administering to said patient at least 150 mg/day of Compound I or a pharmaceutically acceptable salt thereof, and at least 50 mg/day of ritonavir or a pharmaceutically acceptable salt.

5. The method of claim 4, wherein said method comprises administering to said patient 200 mg/day of Compound I or a pharmaceutically acceptable salt thereof, and 100 mg/day of ritonavir or a pharmaceutically acceptable salt.

6. The method of claim 4, further comprising administering to said patient another anti-HCV agent selected from: a HCV polymerase inhibitor, a NS5A inhibitor, a cyclophilin inhibitor, a CD81 inhibitor, or an internal ribosome entry site inhibitor.

7. A method of treating a HCV patient having non-CC IL28B rs12979860 genotype, comprising administering to said patient at least 150 mg/day of Compound I or a pharmaceutically acceptable salt thereof, and at least 50 mg/day of ritonavir or a pharmaceutically acceptable salt.

8. The method of claim 7, wherein said method comprises administering to said patient 200 mg/day of Compound I or a pharmaceutically acceptable salt thereof, and 100 mg/day of ritonavir or a pharmaceutically acceptable salt.

9. The method of claim 7, further comprising administering to said patient another anti-HCV agent selected from: a HCV polymerase inhibitor, a NS5A inhibitor, a cyclophilin inhibitor, a CD81 inhibitor, or an internal ribosome entry site inhibitor.

* * * * *